United States Patent [19]

Shinohara et al.

[11] Patent Number: 5,329,014

[45] Date of Patent: * Jul. 12, 1994

[54] METHOD FOR RECOVERING OPTICALLY ACTIVE TRYPTOPHAN

[75] Inventors: Toru Shinohara; Masaru Otani, both of Saga, Japan

[73] Assignee: Ajinomoto Co., Inc., Tokyo, Japan

[ * ] Notice: The portion of the term of this patent subsequent to Dec. 3, 2008 has been disclaimed.

[21] Appl. No.: 738,446

[22] Filed: Jul. 31, 1991

[30] Foreign Application Priority Data

Aug. 1, 1990 [JP] Japan .................... 2-204388

[51] Int. Cl.$^5$ ............ C07D 209/20; C12P 13/22
[52] U.S. Cl. ....................... 548/498; 23/298; 548/497; 548/499
[58] Field of Search ............ 23/298; 435/108; 548/499, 497, 498

[56] References Cited

U.S. PATENT DOCUMENTS

| 3,825,559 | 7/1974 | Tazuke et al. | 548/498 |
| 4,588,818 | 5/1986 | Kaneko et al. | 548/498 |
| 4,820,825 | 4/1989 | Ootani et al. | 548/496 |
| 5,070,208 | 12/1991 | Yarita et al. | 548/497 |

FOREIGN PATENT DOCUMENTS

| 58-00895 | 1/1983 | Japan | 435/108 |
| 60-04168 | 1/1985 | Japan | 548/497 |
| 60-34196 | 2/1985 | Japan | 435/108 |
| 62-16498 | 1/1987 | Japan | 560/41 |

OTHER PUBLICATIONS

Sienko, M. J. et al. "Chemistry", 2nd ed. McGraw-Hill: New York (1961), p. 346.

Primary Examiner—Gary P. Straub
Assistant Examiner—Peter T. DiMauro
Attorney, Agent, or Firm—Oblon, Spivak, McClelland, Maier & Neustadt

[57] ABSTRACT

Optically active tryptophan of high purity can be obtained in high yields from a tryptophan fermentation broth, using crystallization of optically active tryptophan hydrochloride in combination with concurrent neutralization crystallization. According to the present invention, optically active tryptophan from a tryptophan containing fermentation broth, is carried out by (a) removing cells from the fermentation broth, adding hydrochloric acid, or a mixture of hydrochloric acid and an inorganic salt which contains chloride ions, to the cell-free broth to effect crystallization, (b) separating optically active tryptophan hydrochloride, (c) dissolving the optically active tryptophan hydrochloride, and (d) subjecting the resulting solution and an alkali solution to concurrent neutralization crystallization, maintaining a pH of the crystallization solution in the range of from 3 to 8.

6 Claims, No Drawings

METHOD FOR RECOVERING OPTICALLY ACTIVE TRYPTOPHAN

BACKGROUND OF THE INVENTION

1. Field of the Invention

The present invention relates to a method for recovering optically active tryptophan from a fermentation broth or solution containing the same.

2. Description of Prior Art

Optically active tryptophan has been produced by use of tryptophan-producing bacterial belonging to the genus Bacillus, the genus Brevibacterium, the genus Corynebacterium, the genus Arthrobacter, and other genera, using glucose or the like as a main starting material. However, crude crystals of optically active tryptophan obtained by conventional methods contain impurities such as proteins, coloring matter, etc.

These impurities are generally very hydrophobic, so that even though recrystallization is performed in a conventional manner, the impurities are attracted to the surface of hydrophobic tryptophan crystals, or are occluded onto these crystals. Even if the amount of the impurities is small, purification is difficult. To remove these impurities, the prior art has suggested several methods including:

(1) contacting a solution of crude tryptophan crystals with a nonionic exchange resin to adsorb the impurities onto the resin, and then filtering through an ultrafiltration membrane (Japanese Patent Unexamined Published Application No. 58-895); or (2) heating a tryptophan enzyme reaction solution at 95 to 100° C. in the presence of activated carbon under acidic pH conditions, then performing a solid-liquid separation, contacting the filtrate containing tryptophan with a non-polar porous resin to concentrate and then adding an aliphatic lower alcohol (Japanese Patent Unexamined Published Application No. 61-126070); or (3) adjusting the pH of a tryptophan-containing solution to an alkaline region upon crystallization and performing neutralization crystallization in the presence of a lower alcohol or ketone (Japanese Patent Unexamined Published Application Nos. 59-39857, 60-30694 and 61-12607); etc.

However, none of these methods for purification have proven to be completely satisfactory because:

(1) Since tryptophan is molecularly adsorbed onto resins due to its specific affinity, attributable to its molecular structure, tryptophan has a tendency to be adsorbed and desorbed together with such impurities as coloring matters, etc. It is quite complicated to separate these impurities, and hence, the yield is adversely affected.

(2) Tryptophan has an indole ring which is structurally unstable. If one tries to remove the impurities with any process employing high temperatures, degradation can occur.

(3) Crystallization of tryptophan using an organic solvent is not efficient, since impurities are not easily removed. Further, it is complicated and dangerous to handle and recover organic solvents.

SUMMARY OF THE INVENTION

Accordingly, it is an object of the present invention to provide a simple method for recovery of optically active tryptophan.

It is a further object of the present invention to provide a method for recovery of optically active tryptophan at a high recovery rate and in high purity.

It is a further object of the present invention to provide a method for recovery of optically active tryptophan in high yields.

This and other objects have been attained by providing a process whereby optically active tryptophan of high purity can be obtained in high yields from a tryptophan fermentation broth, using crystallization of optically active tryptophan hydrochloride in combination with concurrent neutralization crystallization. According to the present invention, optically active tryptophan from a tryptophan containing fermentation broth, is carried out by (a) removing cells from the fermentation broth, adding hydrochloric acid, or a mixture of hydrochloric acid and an inorganic salt which contains chloride ions, to the cell-free broth to effect crystallization, (b) separating optically active tryptophan hydrochloride, (c) dissolving the optically active tryptophan hydrochloride, and (d) subjecting the resulting solution and an alkali solution to concurrent neutralization crystallization, maintaining a pH of the crystallization solution in the range of from 3 to 8.

The cells may be removed by use of centrifugation, filtration under pressure, filtration under reduced pressure, filtration through a membrane, e.g., precise filtration, ultrafiltration or other known methods, but ultrafiltration in which cells and protein are simultaneously removed is preferred. The pH of the solution from which the cells are removed is not critical, but is preferably in the acidic region, more preferably from 3 to 5, taking into account removal of cells, protein, etc. by flocculation.

It is preferred that the concentration of optically active tryptophan in the cell-free solution be 50 g/l or greater. When the concentration is less than 50 g/l, the solution is generally not concentrated enough for successful separation and/or crystallization. The technique for concentration is not critical, and conventional techniques are adequate. For example, concentration may be performed by heat under reduced pressure, by freezing, by use of a reverse osmosis membrane, or combinations thereof, in a continuous system. However, for best results, the concentration should be carried out desirably at 80° C. or lower, preferably at 60° C. or lower, since heating at high temperatures can cause decomposition of the tryptophan and formation of colored materials.

Next, hydrochloric acid, either alone or in a mixture with an inorganic salt containing chloride ion, is added upon crystallization of optically active tryptophan from the solution containing at least 50 g/l of optically active tryptophan. Where hydrochloric acid alone is added, it is preferred to add at least 2 equivalents, based on the amount of optically active tryptophan. Where a mixture of hydrochloric acid and the inorganic salt containing chloride ion is added, it is preferred to use at least 1 equivalent of hydrochloric acid and at least 1 equivalent of the inorganic salt containing chloride ion, based on the amount of optically active tryptophan. Suitable inorganic salts include any of the water-soluble salts such as sodium chloride, potassium chloride, etc.

Crystallization of the optically active tryptophan hydrochloride may be performed by crystallization through concentration, cooling crystallization, etc., or combinations thereof, in batch or continuous systems.

The degree of concentration, cooling temperature, cooling rate, etc. are conventionally determined.

After the crystallization, the crystals are separated by centrifugal force or the like. The obtained crystal structures are prismatic in shape.

The optically active tryptophan hydrochloride is then dissolved in water. In this case, the concentration of the optically active tryptophan hydrochloride is preferably set at 50 g/l or more. The solution is subjected to concurrent neutralization crystallization (later described), wherein the pH of the crystallization slurry, which comprises a mixture of an alkali solution with the crystallization solution, is maintained in the range of from 3 to 8, in which the optically active tryptophan is simultaneously crystallized and neutralized.

The alkali solution used herein to neutralize the optically active tryptophan hydrochloride is preferably of an inorganic type, from an economical viewpoint. Examples of the alkali solution include an aqueous sodium hydroxide solution, ammonia water, and the like. The concentration of the alkali solution is not particularly limited.

Concurrent neutralization crystallization comprises simultaneously adding a solution of the optically active tryptophan hydrochloride and an alkali solution, both in small portions, into a crystallization tank or crystallization can, so that the pH during and/or after crystallization is maintained in the range of from 3 to 8. Seed crystals may be added at the beginning of concurrent neutralization crystallization, or alternatively, crystallization may be spontaneously initiated by regulating the rate of neutralization (rate of concurrently feeding the solution of optically active tryptophan hydrochloride and the alkali solution) so that seed crystals are formed immediately upon mixing the solutions. It is generally advantageous that the rate of neutralization crystallization be slow, although it depends on the scale of crystallization. On a scale of approximately 0.1 to $10^5$ liters, it is generally sufficient to feed the solutions into the crystallization tank for from 1 to 4 hours. In order to prevent the decomposition of the tryptophan, the crystallization temperature is preferably maintained at from 20° to 60° C., most preferably at from 30° to 50° C.

After the solution of optically active tryptophan hydrochloride and the alkali solution are fed into the crystallization tank under the conditions for concurrent neutralization crystallization, it is preferred to further cool the crystallization slurry, in order to improve the yield (recovery rate) of the optically active tryptophan crystals.

The crystals of optically active tryptophan precipitated by concurrent neutralization crystallization are isolated by conventional solid-liquid separation. It is particularly preferred to use a centrifuging machine.

The optically active tryptophan is obtained in high yields and high purity by the present method. In order to obtain optically active tryptophan having a purity of 90% or more from a fermentation broth, prior methods have employed complicated operations, such as steps using resin, etc. Where crystals of optically active tryptophan are directly obtained by crystallization, prior methods have recovered about 50 to about 70% of crystals of low purity from the fermentation broth. However, according to the present method, optically active tryptophan having a purity of 90% or more can be obtained in a yield of 70% or higher.

Other features of the invention will become apparent in the course of the following description of exemplary embodiment which is given for illustrative purposes only, and is not intended to be limiting thereof.

EXAMPLE

The pH of 30 l of L-tryptophan fermentation broth was adjusted to 3.5 with 35% hydrochloric acid. After the cells were removed from the broth by centrifugation, the solution was concentrated at a temperature of 60° C. under reduced pressure, until the concentration of L-tryptophan reached 180 g/l. Next, 3.5 equivalents of 35% hydrochloride acid and 3 equivalents of sodium chloride (both relative to the amount of L-tryptophan) were added to the slurry, while keeping the concentrated slurry at 50° C. After cooling to 15° C. overnight, the crystals were separated with a centrifuging machine, and were washed with water. The crystals were dried at 60° C. for 2 hours under reduced pressure to give 156 g of L-tryptophan hydrochloride crystals. The L-tryptophan hydrochloride crystals thus obtained had a purity of 95.7%.

An aqueous solution of 130 g of the L-tryptophan hydrochloride crystals at a concentration of 150 g/l and 27% aqueous sodium hydroxide solution were simultaneously fed into a crystallization tank at 30° C., while controlling the feeding rate of each solution so that the pH of the crystallization slurry was maintained at 6.5. After addition of the solution of L-tryptophan hydrochloride was completed, the crystallized L-tryptophan was isolated with a centrifuging machine. The crystals were then washed with water, and dried at 60° C. for 2 hours under reduced pressure to give 92 g of L-tryptophan crystals. The L-tryptophan crystals thus obtained had a purity of 96.4%, corresponding to a yield of 75% of L-tryptophan from that produced in the fermentation broth.

COMPARATIVE EXAMPLE 1

The pH of 30 l of L-tryptophan fermentation broth was adjusted to 3.5 with 35% hydrochloric acid. After the cells were removed from the broth by centrifugation, the solution was concentrated at 60° C. under reduced pressure until the concentration of L-tryptophan reached 180 g/l. Next, 5 equivalents of 35% hydrochloric acid were added to the crystallization slurry (relative to the amount of L-tryptophan), while the slurry was maintained at a temperature of 50° C. After cooling to 15° C. overnight, the crystals were separated with a centrifuging machine, and washed with water. The crystals were dried at 60° C. for 2 hours under reduced pressure to give 161 g of L-tryptophan hydrochloride crystals. The L-tryptophan hydrochloride crystals had a purity of 95.7%.

After a crystallization tank was charged with an aqueous solution of 130 g of the thus obtained L-tryptophan hydrochloride in a concentration of 150 g/l, neutralization crystallization was performed by adding dropwise thereto a 27% aqueous sodium hydroxide solution while stirring at 30° C. until the pH reached 6.5. The crystals were so finely divided, the operations for stirring, separation and the like became impossible.

COMPARATIVE EXAMPLE 2

The pH of an L-tryptophan fermentation broth was adjusted to 3.5 with 35% hydrochloric acid. After the cells were removed from the broth by centrifugation, the solution was concentrated at a temperature of 60° C. under reduced pressure until the concentration of L-tryptophan reached 150 g/l. After cooling the concentrated slurry to 15° C. overnight, the crystals were separated with a centrifuging machine, and were washed with water. The crystals were dried at 60° C. for 2 hours under reduced pressure to give 106 g of L-tryptophan hydrochloride crystals. The L-tryptophan hydrochloride crystals were obtained in a yield of 60%, and had a purity of 71.8%.

EFFECTS OF THE INVENTION

As stated above, optically active tryptophan crystals of high purity can be precipitated by the crystallization treatment of the present invention in a high recovery rate, without performing treatment steps with a resin or large quantities of an organic solvent. Waste liquids accompanied by the treatment with a resin are not generated in the present invention, and therefore, the present invention is environmentally effective.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A method for recovering optically active tryptophan from a fermentation broth comprising optically active tryptophan, which comprises:
   (i) removing cells from said fermentation broth comprising optically active tryptophan to obtain a cell-free fermentation broth comprising optically active tryptophan and proteins;
   (ii) adding (a) hydrochloric acid or (b) a mixture of hydrochloric acid and an inorganic salt containing chloride ion to said cell-free fermentation broth obtained in step (i) to precipitate and separate optically active tryptophan hydrochloride from said cell-free fermentation broth and to obtain separated optically active tryptophan hydrochloride;
   (iii) dissolving said separated optically active tryptophan hydrochloride, to obtain a solution comprising said optically active tryptophan hydrochloride;
   (iv) subjecting said solution comprising said optically active tryptophan hydrochloride to concurrent neutralization crystallization by simultaneously adding said solution of optically active tryptophan hydrochloride and an alkali solution, into a crystallizer while maintaining the pH in a range of from 3 to 8; and
   (v) isolating optically active tryptophan crystals thereof.

2. The method of claim 1, further comprising concentrating said cell-free broth, such that said optically active tryptophan is present in a concentration of at least 50 g/l, said concentrating step being performed after said adding step.

3. The method of claim 1, wherein hydrochloric acid is added in said adding step (ii) and said hydrochloric acid is added in an amount of at least 2 equivalents, relative to said optically active tryptophan.

4. The method of claim 1, wherein a mixture of hydrochloric acid and an inorganic salt containing chloride ion is added in said adding step (ii) and said mixture of hydrochloric acid and inorganic salt containing chloride ion is added in an amount of at least 1 equivalent of hydrochloric acid and at least 1 equivalent of said chloride ion, relative to said optically active tryptophan.

5. The method of claim 1, wherein said solution comprising said optically active tryptophan hydrochloride contains said optically active tryptophan hydrochloride in a concentration of at least 50 g/l.

6. The method of claim 1, wherein said optically active tryptophan crystals are isolated by centrifugal separation.

* * * * *